(12) United States Patent
Uchiyama et al.

(10) Patent No.: US 9,285,344 B2
(45) Date of Patent: Mar. 15, 2016

(54) DISCHARGE IONIZATION CURRENT DETECTOR AND GAS CHROMATOGRAPH

(71) Applicant: SHIMADZU CORPORATION, Kyoto-shi, Kyoto (JP)

(72) Inventors: Shinji Uchiyama, Kyoto (JP); Yasunori Terai, Ibaraki (JP)

(73) Assignee: SHIMADZU CORPORATION, Kyoto (JP)

( * ) Notice: Subject to any disclaimer, the term of this patent is extended or adjusted under 35 U.S.C. 154(b) by 226 days.

(21) Appl. No.: 13/846,874

(22) Filed: Mar. 18, 2013

(65) Prior Publication Data

US 2014/0070814 A1    Mar. 13, 2014

(30) Foreign Application Priority Data

Sep. 13, 2012  (JP) ................................ 2012-201348

(51) Int. Cl.
  *G01N 27/62* (2006.01)
  *G01N 27/66* (2006.01)
  *G01N 30/64* (2006.01)

(52) U.S. Cl.
  CPC ............. *G01N 27/66* (2013.01); *G01N 30/64* (2013.01)

(58) Field of Classification Search
  CPC ....... G01N 30/64; G01N 27/66; G01N 27/62; G01N 27/68; G01N 27/70; G01N 2030/642
  USPC ........................................... 324/464
  See application file for complete search history.

(56) References Cited

U.S. PATENT DOCUMENTS 4,555,383 A  * 11/1985 Hall ................................ 422/89
5,028,544 A    7/1991 Rasulev et al.
2011/0187379 A1 * 8/2011 Shinada et al. ............... 324/464

FOREIGN PATENT DOCUMENTS

| FI | 884718 A | 4/1989 |
|---|---|---|
| JP | 2010-002420 A | 1/2010 |
| JP | 2010-060354 A | 3/2010 |

OTHER PUBLICATIONS

Office Action Chinese Patent Application No. 201310110175.3 dated Oct. 23, 2014.

* cited by examiner

*Primary Examiner* — Son Le
(74) *Attorney, Agent, or Firm* — McDermott Will & Emery LLP

(57) ABSTRACT

To provide a discharge ionization current detector 3, where a partition 13a in which a through hole for penetrating a tubule 24 for introducing a sample gas is created is provided between a collector electrode 20 and an outlet for discharging a gas 26 so that a gas for generating plasma that has been generated by electrodes for discharge 15, 16 and 17 passes through a gap between the through hole and the tubule 24 so as to be directed towards the outlet for discharging a gas, and thus, the air that has entered from the other side 25 of the partition cannot pass through the through hole in the opposite direction.

6 Claims, 4 Drawing Sheets

DISCHARGE IONIZATION CURRENT DETECTOR AND GAS CHROMATOGRAPH

RELATED APPLICATIONS

This application claims the benefit of Japanese Application No. 2012-201348, filed on Sep. 13, 2012, the disclosures of which Applications are incorporated by reference herein.

TECHNICAL FIELD

The present invention relates to a discharge ionization current detector using a low frequency barrier discharge, and a gas chromatograph using this detector.

BACKGROUND ART

Various types of detectors, such as a thermal conductivity detector (TCD), an electron capture detector (ECD), a flame ionization detector (FID) and a flame photometric detector (FPD), have been put into practice as detectors for a gas chromatograph. From among these detectors, in particular, FIDs have been often used as a detector for detecting an organic substance. FIDs are a type of detector where sample molecules in a sample gas are ionized by a hydrogen flame and the ionization current is measured so as to provide a wide, dynamic range (see Patent Document 1). However, FIDs have such defects that a sufficiently low lower limit for detection cannot be gained due to the low efficiency in ionization, and in particular, the efficiency of ionization for alcohols, aromatics and chlorine-based substances is low, and furthermore, it is necessary to provide a special facility, such as an explosion-proof facility, because of its need for hydrogen, which makes handling troublesome.

In addition, pulse discharge detectors (PDD) have been known as a conventional detector that can detect, with high sensitivity, inorganic substances and organic compounds having a low boiling point. PDDs are a type of detector that excites helium molecules through a pulse discharge under high pressure, ionizes the molecules to be measured using light energy generated when the helium molecules in the excited state return to the ground state, and measures the ion current resulting from ionization. Accordingly, the PDD is easy to handle as compared to the FID because it does not use hydrogen. In addition, its efficiency of ionization is high as compared to that of the FID. However, the PDDs have such problems that the ionization is uneven and the dynamic range is narrow due to the instability of the plasma for ionization, and furthermore, a problem arises in that the electrodes and the like may be damaged due to high temperature plasma.

In order to solve these problems with the conventional detectors, a detector using a dielectric barrier discharge using low frequency, that is to say, a discharge ionization current detector or a detector that is referred to as a barrier discharge ionization detector (BID), has been proposed (see Patent Document 2).

FIG. 4 is a longitudinal cross-sectional diagram showing an example of the structure of a conventional discharge ionization current detector. One side of the tubular body 41 for forming the main body of the detector is formed of a crystal tube 42, and electrodes for discharge 43 to 45 are provided around the outer periphery of the crystal tube 42. An inlet for introducing a gas for generating plasma 46, through which a gas for generating plasma, such as helium, is introduced, is created at one end of the crystal tube 42. A bias electrode 47 and a collector electrode 48 are formed on the inner surface of the tubular body 41 on the side opposite to the crystal tube 42.

In addition, an outlet for discharging a gas 49 is created in the sidewall of the tubular body 41 on the side opposite to the crystal tube 42 and further away than the collector electrode 48. In addition, a tubule 50 for introducing a sample gas to be measured is inserted through the other end of the tubular body 41. This tubule 50 is an end through which a sample gas flows out of the column in the case where the system is used as the detector for a gas chromatograph. Furthermore, this tubule (column end) 50 is connected to the tubular body 41 through a removable tube joint that can make tight sealing and connection possible, typically a ferrule joint 51.

In the above-described structure, a high voltage with low frequency is applied to the electrode 44 for discharge while introducing a gas for generating plasma into the tubular body 41 through the inlet for introducing a gas for generating plasma 46, and at the same time, the electrodes for discharge 43 and 45 are grounded so that a low frequency, alternating current exciting dielectric barrier discharge is generated and the gas for generating plasma is partially converted to plasma. In this state, a sample gas is introduced into the tubular body 41 through the tubule 50, and then, the component molecules of the sample gas are ionized due to the effects of the light released from the plasma or the excited species of helium. These ions are attracted to the bias electrode 47 to which a direct current bias voltage is applied, and furthermore are collected by the collector electrode 48, and thus, the ionization current is detected by a detector circuit that includes a current amplifier connected to the collector electrode 48.

The plasma under atmospheric pressure that is generated through the above-described low frequency, alternating current exciting dielectric barrier discharge is a non-equilibrium plasma where the neutral gas temperature is very low, and therefore, no such problems arise that an electrode is damaged due to the temperature, unlike the above, or the ionization becomes uneven due to the instability of the plasma.

PRIOR ART DOCUMENTS

Patent Documents

Patent Document 1: Japanese Unexamined Patent Publication 2010-002420
Patent Document 2: Japanese Unexamined Patent Publication 2010-060354

SUMMARY OF THE INVENTION

Problem to be Solved by the Invention

In the tubular body 41 in conventional discharge ionization current detectors, a ferrule joint 51, which is a tube joint that can be relatively easy to remove and attach, is used for a tubule (column end) for introducing a sample gas because of the structure or the like of a gas chromatograph. That is to say, the gas chromatograph is roughly formed of a sample evaporation chamber, a column and a detector, where it is necessary to connect the column and the detector to each other as well as the column and the sample evaporation chamber, and in addition, it is necessary to replace the column properly according to the circumstances. Accordingly, for these connection portions, a joint that makes removal and attachment relatively easy should be used.

Here, the discharge ionization current detectors using a low frequency, alternating current exciting dielectric barrier discharge have extremely high sensitivity, and therefore, air that enters from the outside to the vicinity of the collector electrode 48 within the tubular body 41 could cause noise.

In the airtight structure where the tubule 50 for introducing a sample gas into the tubular body 41 is connected using a ferrule joint 51 made of a ferrule and a nut, it is difficult to completely prevent air from entering into the inside at all times. In the structure of the conventional discharge ionization current detector in FIG. 4, some components of the air that has entered into the inside reach the collector electrode 48, and thus, such a problem arises that noise is caused by the introduction of air.

The present invention is provided in view of these problems, and an object thereof is to provide a discharge ionization current detector where noise is not caused in the output of the detector even when a small amount of air enters through the connection portion between the tubular body that forms the detector and the tubule for introducing a sample gas into the tubular body.

Means for Solving Problem

In order to achieve the above-described object, the discharge ionization current detector according to the present invention is a discharge ionization current detector for detecting an ion current by introducing a sample gas into a tubular body through a tubule, the tubular body having at a first end a cylindrical dielectric around the outer periphery of which an electrode for discharge is formed, and the tubule for introducing a sample gas being inserted into the tubular body at a second end, by ionizing the above-described sample gas using plasma that has been generated by applying a low frequency, alternating current voltage to the above-described electrode for discharge while allowing a gas for generating plasma to flow through the above-described first end, and at the same time by collecting the resulting ions around a collector electrode provided closer to the above-described second end than the above-described electrode for discharge, and is characterized in that an outlet for discharging a gas is created in the above-described tubular body at a point closer to the above-described second end than the above-described collector electrode, and a partition is provided between the outlet for discharging a gas and the above-described collector electrode in the direction in which the tubular body is crossed so that the above-described tubule penetrates through a through hole created in the partition, and the opening at one end of the tubule is located closer to the above-described first end than the partition.

Here, according to the present invention, such a structure that a cylindrical portion that protrudes towards the above-described second end is formed on the above-described partition in a location that surrounds the above-described through hole, and the above-described tubule penetrates through the above-described through hole by passing through the inside of the cylindrical portion can be appropriately adopted.

In addition, according to the present invention, such a structure that the above-described tubule is connected to an opening created in the above-described tubular body on the above-described second end side by means of a ferrule joint, and the above-described outlet is created in a sidewall of the above-described tubular body can be adopted.

The gas chromatograph according to the present invention is a gas chromatograph for detecting a sample gas that has been introduced through a gas introduction portion by allowing the sample gas to flow into a column together with a carrier gas and by using a detector to ionize the sample gas of which the components have been separated by stationary phases within the column, and is characterized in that the discharge ionization current detector is used as the above-described detector, and the end of the above-described column through which the sample gas flows out is inserted into the above-described tubular body as the above-described tubule.

In order to solve the problems, the present invention provides such a structure of the detector that a small amount of air that has entered into the tubular body of the detector through the connection portion between the tubular body and the tubule for introducing a sample gas, such as a column end, can be discharged to the outside through the outlet for discharging a gas without the air that had entered reaching the collector electrode.

That is to say, the gas for generating plasma that has been introduced through one end of the tubular body passes through the region for generating plasma with electrodes for discharge and creates flow towards the outlet for discharging a gas provided at a point closer to the other end than the collector electrode. When a partition in which a through hole for penetrating a tubule for introducing a sample gas is created is provided between the collector electrode and the outlet for discharging a gas, the gas for generating plasma passes through a gap between the through hole and the tubule so as to be directed towards the outlet for discharging a gas. Namely, the flow path of the gas for generating plasma is partially narrowed, and the speed of the flow of the gas increases through this portion due to the orifice effect, even if the amount of flow is very small. Accordingly, the air that has entered from the other side of the partition cannot pass through the through hole in the opposite direction due to the existence of the gas flow that passes through the through hole and is directed towards the outlet, and thus is prevented from reaching the vicinity of the collector electrode.

When a cylindrical portion that protrudes towards the other end side of the tubular body is provided in addition to a partition so as to surround the through hole in the partition, the cylindrical portion is filled in with a gas flow that flows fast through the through hole, and the air that has entered is further prevented from approaching the through hole.

In the typical structure of the present invention, the tubule for introducing a sample gas is connected to the opening created at the other end of the tubular body through a ferrule joint, and the outlet for discharging a gas is created in the sidewall of the tubular body.

Effects of the Invention

In the discharge ionization current detector according to the present invention, even if a small amount of air enters through the connection portion between the tubule, such as a column end for introducing a sample gas, and the tubular body that is the main body of the detector, the air is discharged through the outlet for discharging a gas in the tubular body without reaching the vicinity of the collector electrode, and therefore does not cause noise.

In addition, the gas chromatograph according to the present invention uses a discharge ionization current detector with high sensitivity, where a low frequency, alternating current exciting dielectric barrier discharge is used to provide uniform ionization, and furthermore, a tube joint that can be easily removed or attached, such as a conventional ferrule joint, is used for the connection between the detector and the column, and as a result, measurement of a high S/N with high sensitivity can be carried out without causing noise to the detection results even when air enters through the connection portion.

PREFERRED EMBODIMENTS OF THE INVENTION

In the following, the embodiments of the present invention are described in reference to the drawings.

Figure 1:
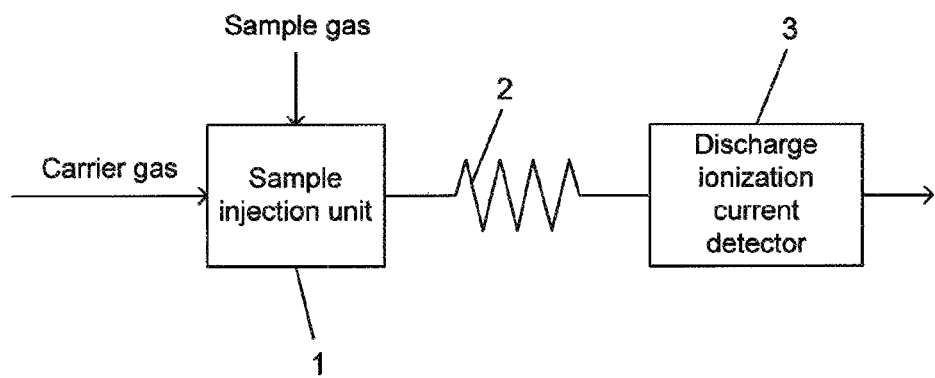
FIG. 1 is a schematic diagram showing the structure of the gas chromatograph according to an embodiment of the present invention.
Figure 2:
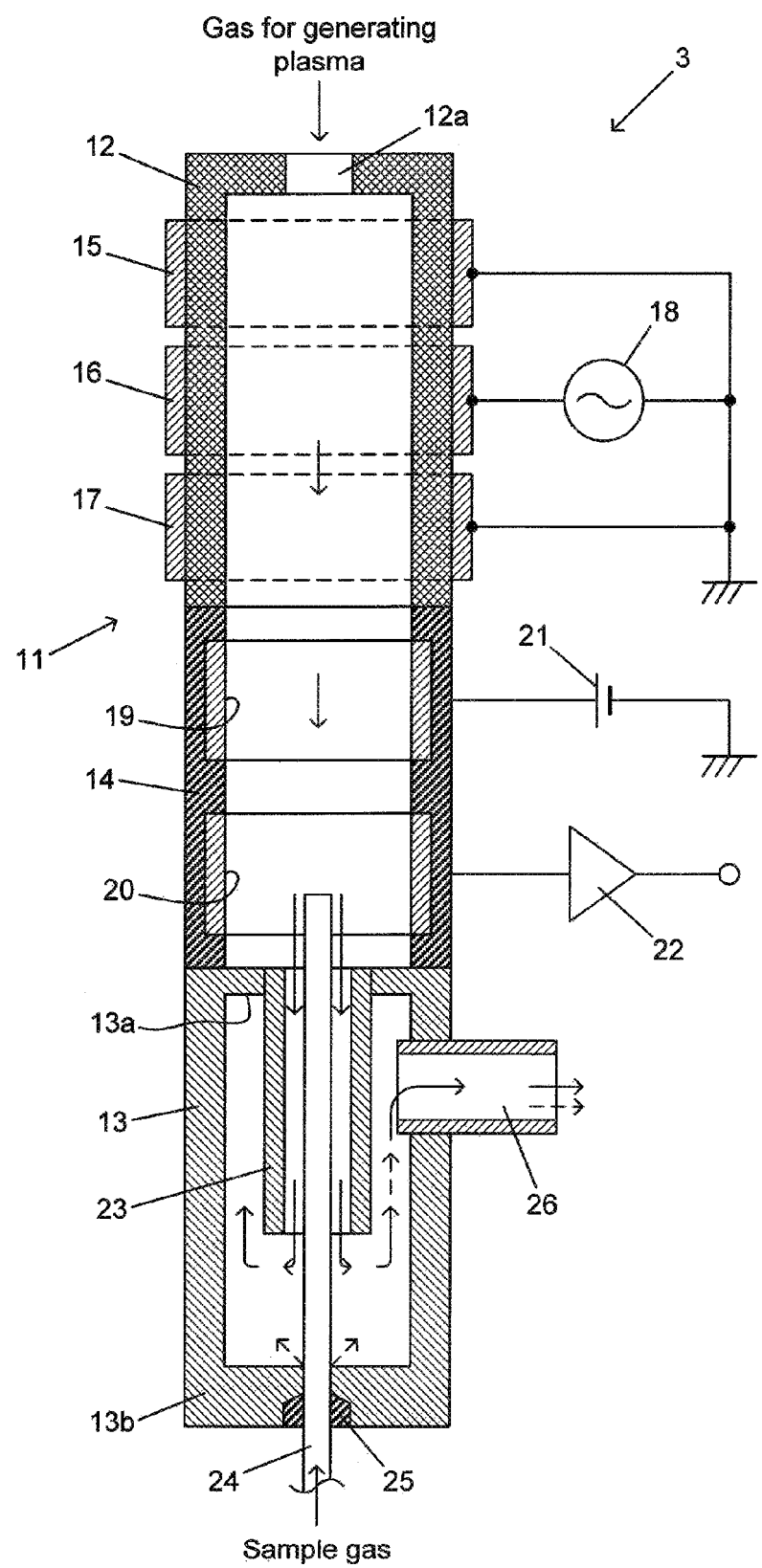
FIG. 2 is a longitudinal cross-sectional diagram showing the structure of the discharge ionization current detector in FIG. 1.
Figure 4:
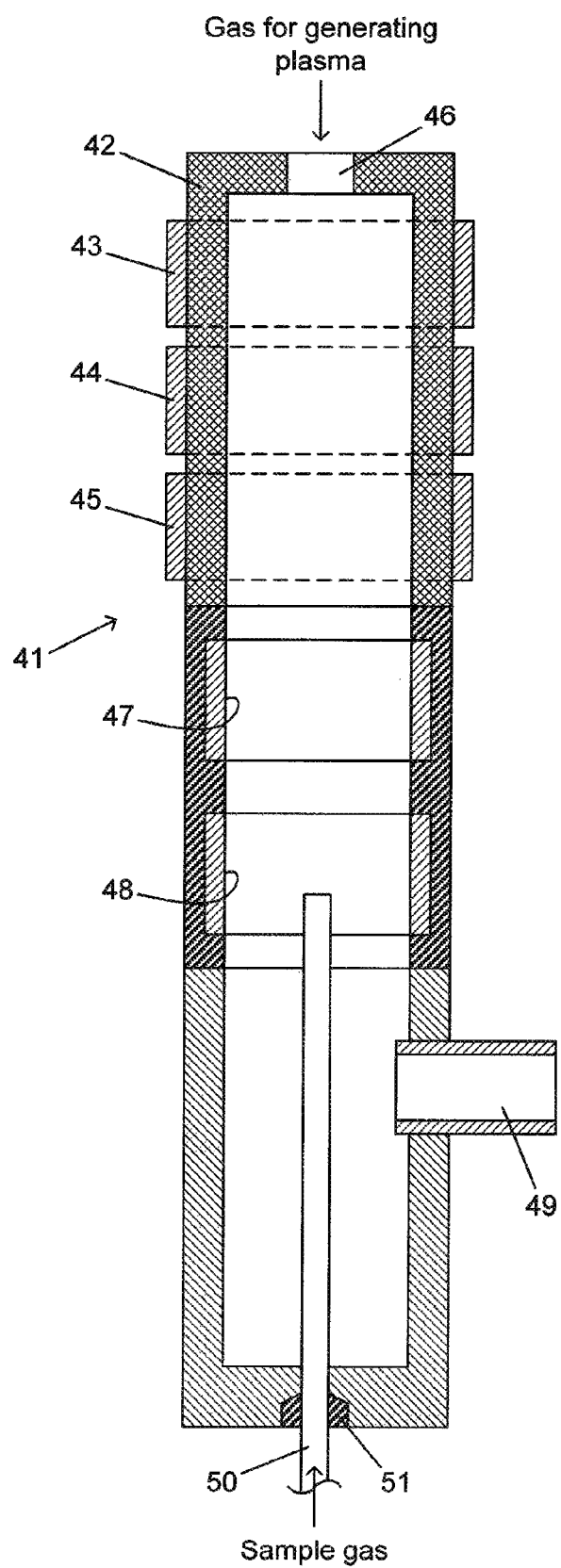
FIG. 4 is a longitudinal cross-sectional diagram showing an example of the structure of a conventional discharge ionization current detector.

FIG. 1 is a schematic diagram showing the structure of the gas chromatograph according to one embodiment of the present invention, and FIG. 2 is a longitudinal cross-sectional diagram showing the structure of the discharge ionization current detector, like the one in FIG. 4.

The gas chromatograph according to this embodiment is mainly formed of a sample injection unit 1 for injecting a sample gas, a column 2 through which a sample gas that has been injected from this sample injection unit 1 flows together with a carrier gas, and a discharge ionization current detector 3 for ionizing and detecting the gas of which the components are chronologically separated through the column 2. This embodiment is characterized by the structure of the discharge ionization current detector 3 of which the structure is described below in detail in reference to FIG. 2.

The main body of the discharge ionization current detector 3 is formed of a tubular body 11, and one side thereof (upper side in the figure) is formed of a crystal tube 12, the other side thereof (lower side in the figure) is formed of a metal tube 13, such as of stainless steel, and the middle portion is formed of an insulator tube 14, such as of ceramic.

The outer periphery of the crystal tube 12 is provided with three electrodes for discharge 15, 16 and 17 at a predetermined distance away from each other. From among these electrodes for discharge 15, 16 and 17, an alternating current power supply for excitation 18 is connected to the electrode for discharge 16 at the center, and the electrodes for discharge 15 and 17 at the two sides are grounded. An alternating current power supply for excitation 18 generates a low frequency, high alternating current voltage having a frequency of 1 kHz to 100 kHz and a voltage (total amplitude) of approximately 1 kV to 10 kV. In addition, an inlet for introducing a gas for generating plasma 12a through which a gas for generating plasma, such as helium, is introduced is created at the upper end of the crystal tube 12.

The inner surface of the insulator tube 14 is provided with a bias electrode 19 on the upper side and with a collector electrode 20 on the lower side. A bias direct current power supply 21 is connected to the bias electrode 19, and at the same time, a current amplifier 22 is connected to the current electrode 20.

The metal tube 13 has inner flanges 13a and 13b formed in the two end portions, upper and lower. A cylindrical body 23 made of a metal, for example, is inserted and secured in the opening at the center of the inner flange 13a on the upper side. In addition, a tubule 24, which is an end of the column 2 from which a sample gas flows out, is inserted into the opening at the center of the inner flange 13b on the lower side and air-tightly connected to the tubular body 11 by means of the ferrule joint 25. This tubule 24 penetrates through the cylindrical body 23 so that an end thereof reaches the location in which the collector electrode 20 is formed and has an opening. Furthermore, an outlet for discharging a gas 26 is provided in the sidewall of the metal tube 13, and the above-described cylindrical body 23 reaches a point beneath this outlet for discharging a gas 26.

In the discharge ionization current detector 3 having the above-described structure, a gas for generating plasma, such as helium, is introduced through the opening for introducing a gas for generating plasma 12a during the operation of the gas chromatograph so that a low frequency, alternating current voltage is applied to the electrode for discharge 16 from the alternating current power supply for excitation 18, and at the same time, a bias voltage is applied to the bias electrode 19 from the bias direct current power supply 21. In addition, a sample gas that has been chronologically separated through the column 2 (see FIG. 1) is introduced through the tubule 24.

When a low frequency, alternating current voltage is applied to the electrode for discharge 16, a low frequency, alternating current exciting dielectric barrier discharge is generated so that the gas for generating plasma that has flown into the tubular body 11 is partially converted to plasma. The component molecules of the sample gas that has flown into the tubular body 11 from the tubule 24 through the column 2 together with a carrier gas are ionized due to the effects of the light emitted from plasma and the exciting species of the gas for generating plasma. The resulting ions are attracted to the bias electrode 19 and are collected by the collector electrode 20. The amount of component molecules that have been ionized is outputted as a detection value of the ion current by the current amplifier 22 that is connected to the collector electrode 20.

During the operation of this detector, the gas for generating plasma that has flown into the tubular body 11 from the opening for introducing a gas for generating plasma 12a that has been created at the top of the tubular body 11 flows down through the tubular body 11, as indicated by the solid arrows in FIG. 2, passes through the cylindrical body 23 secured at the center of the inner flange 13a of the metal tube 13 together with the sample gas that been introduced into the tubular body 11 through the tubule 24 so as to flow into the metal tube 13, and then flows out to the outside through the opening for discharging a gas 26 provided in the sidewall of the metal tube 13. This flow is accelerated at the same time as it goes into the cylindrical body 23 having a diameter smaller than the inner diameter of the crystal tube 12 and the insulator tube 14, and then it goes out of the lower end of the cylindrical body. In the case where air enters through the ferrule joint 25, the gas that has entered diffuses within the metal tube 13, as indicated by the broken arrows in the figure. However, the gas that has entered through the ferrule joint 25 cannot enter into this cylindrical body 23 due to the relatively fast gas flow blowing out from the lower end of the cylindrical body 23 as described above, and therefore is discharged to the outside through the outlet for discharging a gas together with the gas for generating plasma and the sample gas that have flown into the metal tube 13 through the cylindrical body 23.

That is to say, the air that has entered through the ferrule joint 25 is discharged through the outlet for discharging a gas 26 without reaching the detection region that is in the location where the collector electrode 20 is formed. Therefore, the air that has entered does not cause noise to the output of the detector.

Figure 3:
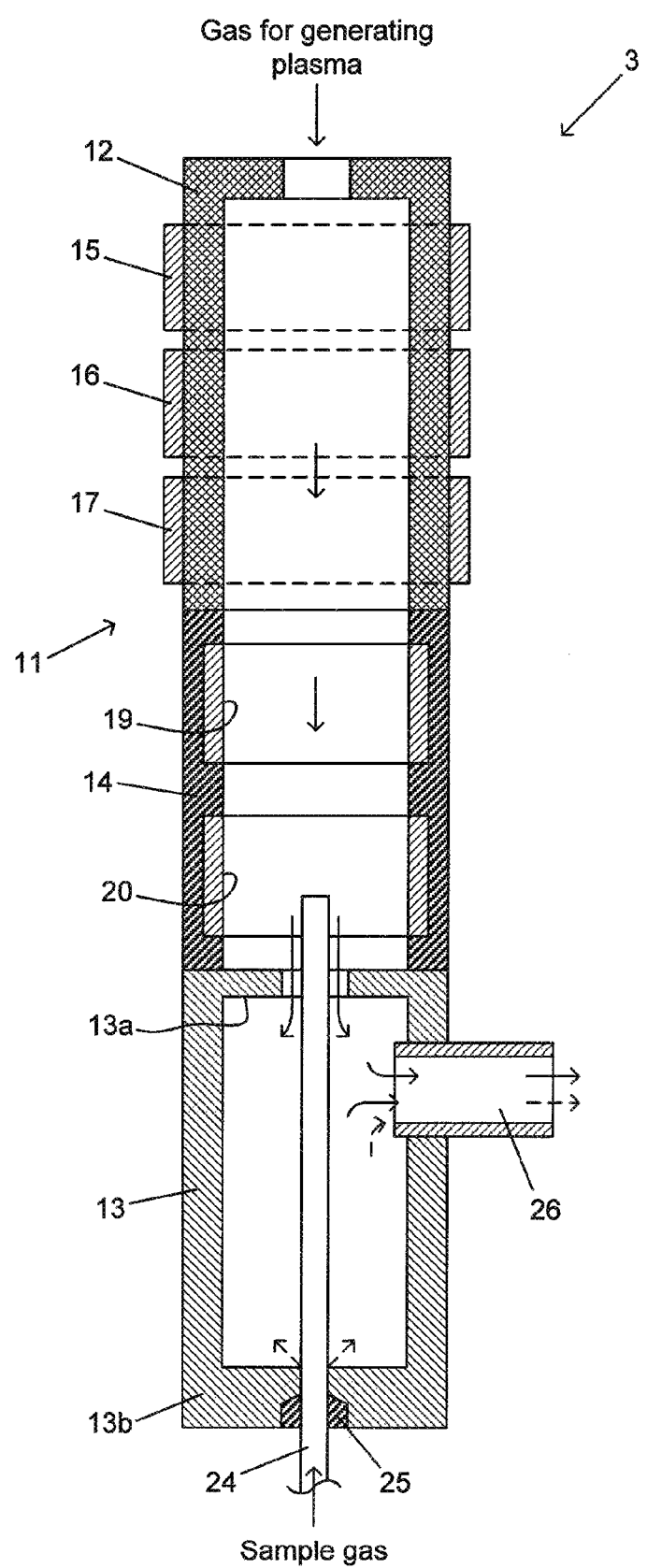
FIG. 3 is a longitudinal cross-sectional diagram showing another example of the structure of the discharge ionization current detector.

Though in the above-described embodiment a structure made of an inner flange 13a of the metal tube 13 and a cylindrical body 23 secured on the inner surface thereof is provided between the collector voltage 20 within the tubular body 11 and the outlet for discharging a gas 26, in other words, a structure having a partition that crosses the tubular body 11 (inner flange 13a), a through hole provided in this partition, and a cylindrical portion (cylindrical body 23) that protrudes from the partition towards the other end side (lower end side) so as to surround the through hole is provided between the collector electrode 20 and the outlet for discharging a gas 26, the present invention is not limited to such an example, and only a partition with a through hole may be formed instead of the above-described structure. An example of this structure is shown in FIG. 3. Here, in FIG. 3, the same symbols are attached to the same members as in FIG. 2, and the descriptions in detail are not repeated below.

The embodiment in FIG. 3 is characterized by the structure that can be compared to that of the previous embodiment in FIG. 2 as follows. The two are the same in that the inner flange 13a of the metal tube 13 on the upper side is used as the partition, but in this embodiment, no cylindrical body 23 as that secured to the inner surface of the inner flange 13a is provided. Here, the inner diameter of the inner flange 13a is the same as the inner diameter of the cylindrical body 23 in the previous embodiment.

In the embodiment in FIG. 3, the gas for generating plasma that has flown into the tubular body 11 through the opening for introducing a gas for generating plasma 12a flows down through the tubular body 11, as indicated by the solid arrows, passes through the inner flange 13a together with a sample gas so as to enter into the metal tube 13, and is discharged to the outside through the outlet for discharging a gas 26 provided in the sidewall of the metal tube 13. The speed of this gas flow increases due to the orifice effect when passing through the inner flange 13a because the inner diameter of this inner flange 13a is smaller than the inner diameter of the crystal tube 12 and the insulator tube 14. That is to say, even if a microscopic amount of gas flows, the speed of the flow is high when flowing into the metal tube 13 through the inner flange 13a. As a result, the gas with air cannot go beyond the inner flange 13a nor enter into the insulator tube 14, but instead is discharged to the outside by the outlet for discharging a gas 26, as indicated by the broken arrows in the figure, even when air enters through the ferrule joint 25. Accordingly, air does not reach the vicinity of the collector electrode 19 and does not cause noise to the output of the detector.

EXPLANATION OF SYMBOLS 1 sample injection unit
2 column
3 discharge ionization current detector
11 tubular body
12 crystal tube
13 metal tube
14 insulator tube
15, 16, 17 electrodes for discharge
18 alternating current power supply for excitation
19 bias electrode
20 collector electrode
21 bias direct current power supply
22 current amplifier
23 cylindrical body
24 tubule
26 outlet for discharging a gas

The invention claimed is:

1. A discharge ionization current detector for detecting an ion current by introducing a sample gas into a tubular body through a tubule, the tubular body having at a first end a cylindrical dielectric around the outer periphery of which an electrode for discharge is formed, and the tubule for introducing a sample gas being inserted into the tubular body at a second end, by ionizing said sample gas using plasma generated by applying a low frequency, alternating current voltage to said electrode for discharge while allowing a gas for generating plasma to flow through said first end, and at the same time by collecting the resulting ions around a collector electrode provided closer to said second end than said electrode for discharge, wherein
the discharge ionization current detector comprises:
an outlet for discharging a gas, created in said tubular body at a point closer to said second end than said collector electrode, and
a partition, provided between the outlet for discharging a gas and said collector electrode in the direction in which the tubular body is crossed, for separating the tubular body into a first chamber on the side of the first end where the sample gas is ionized and a second chamber on the side of the second end, the first chamber having the electrode for discharge and the collector electrode, the second chamber having the outlet for discharging the gas, the partition having a through hole for allowing the first and second chambers to communicate with each other, wherein
the tubule is inserted into the through hole, and an opening at one end of the tubule is located closer to said first end than the partition.

2. The discharge ionization current detector according to claim 1, wherein a cylindrical portion that protrudes towards said second end is formed on said partition in a location that surrounds said through hole, and said tubule penetrates through said through hole by passing through the inside of the cylindrical portion.

3. The discharge ionization current detector according to claim 1 or 2, wherein said tubule is connected to an opening created in said tubular body on said second end side by means of a ferrule joint, and said outlet is created in a sidewall of said tubular body.

4. A gas chromatograph for detecting a sample gas to be introduced through a gas introduction portion by allowing the sample gas to flow into a column together with a carrier gas and by using a detector to ionize the sample gas of which the components are separated by stationary phases within the column, wherein the discharge ionization current detector according to claim 1 is used as said detector, and the end of said column through which the sample gas flows out is inserted into said tubular body as said tubule.

5. A gas chromatograph for detecting a sample gas to be introduced through a gas introduction portion by allowing the sample gas to flow into a column together with a carrier gas and by using a detector to ionize the sample gas of which the components are separated by stationary phases within the column, wherein the discharge ionization current detector according to claim 2 is used as said detector, and the end of said column through which the sample gas flows out is inserted into said tubular body as said tubule.

6. A gas chromatograph for detecting a sample gas to be introduced through a gas introduction portion by allowing the sample gas to flow into a column together with a carrier gas and by using a detector to ionize the sample gas of which the components are separated by stationary phases within the column, wherein the discharge ionization current detector according to claim 3 is used as said detector, and the end of said column through which the sample gas flows out is inserted into said tubular body as said tubule.

\* \* \* \* \*